United States Patent [19]

Liburdy

[11] Patent Number: 4,801,459
[45] Date of Patent: Jan. 31, 1989

[54] TECHNIQUE FOR DRUG AND CHEMICAL DELIVERY

[76] Inventor: Robert P. Liburdy, 1820 Mountain View Dr., Tiburon, Calif. 94920

[21] Appl. No.: 893,436

[22] Filed: Aug. 5, 1986

[51] Int. Cl.$^4$ .................... A61K 9/66; A61K 37/22; B01J 13/02
[52] U.S. Cl. .................... 424/450; 128/804; 264/4.3; 428/402.2; 436/829; 424/1.1
[58] Field of Search .................... 264/4.3; 424/450; 436/829; 128/804

[56] References Cited

U.S. PATENT DOCUMENTS

| | | | |
|---|---|---|---|
| 4,230,129 | 10/1980 | Leveen | 128/804 |
| 4,235,871 | 11/1980 | Papahadjopoulos et al. | 424/92 X |
| 4,341,227 | 7/1982 | Turner | 128/804 |
| 4,425,117 | 1/1984 | Hugemann et al. | 604/93 |
| 4,439,197 | 3/1984 | Honda et al. | 604/891 |
| 4,448,765 | 5/1984 | Ash et al. | 424/14 |
| 4,452,775 | 6/1984 | Kent | 424/19 |
| 4,668,638 | 5/1987 | Janoff et al. | 264/4.6 X |
| 4,670,386 | 6/1987 | Sugaar | 435/29 |

OTHER PUBLICATIONS

Yatvin, Milton B. et al, "Design of Liposomes for Enhanced Local Release of Drugs by Hyperthermia", *Science*, vol. 202, Dec. 22, 1978, pp. 1290–1292.
Weinstein, J. N. et al, "Liposomes and Local Hyperthermia: Selective Delivery of Methotrexate to Heated Tumors", *Science*, vol. 204, Apr. 13, 1979, pp. 188–191.
Liburdy, Robert P. et al, "Microwaves and the Cell Membrane, II Temperature, Plasma and Oxygen Mediate Microwave-Induced Membrane Permeability in the Erythrocyte", *Radiation Research*, 102, 190–205 (1985).
Liburdy, R. P. et al, "Microwave Bioeffects in the Erythrocyte are Temperature and pO$_2$ Dependent: Cation Permeability and Protein Shedding Occur at the Membrane Phase Transition", *Bioelectromagnetics*, 5:283–201 (1984).
Liburdy, R. P.: "Microwave-Stimulated Drug Release from Liposomes", *Radiation Research*, 103, 266–275 (1985).

Primary Examiner—Richard D. Lovering
Attorney, Agent, or Firm—Donald J. Singer; Jacob N. Erlich

[57] ABSTRACT

A technique for rapidly delivering drugs and/or chemicals to a specific area of the body by subjecting a liposome encapsulated drug and/or chemical to nonionizing electromagnetic fields. By subjecting the liposome to such fields in the range of 26–2,450 MHz drug/chemical release occurs in a rapid fashion and at temperatures that the liposomes are normally not leaky. This is a non-thermal effect of the field on the liposome that is not related to heating. Consequently, localized release of drug/chemicals can be effected without subjecting the diseased tissue to adverse heating. In addition, drug/chemical release due to electromagnetic-field treatment of liposomes is enhanced by serum and/or oxygen.

18 Claims, 7 Drawing Sheets

TECHNIQUE FOR DRUG AND CHEMICAL DELIVERY

STATEMENT OF GOVERNMENT INTEREST

The invention described herein may be manufactured and used by or for the Government for governmental purposes without the payment of any royalty thereon.

BACKGROUND OF THE INVENTION

This invention relates generally to a technique for delivering drugs and/or chemicals, and, more particularly, to effecting such delivery by using nonionizing electromagnetic fields (microwave and RF radiation) to release drugs from liposomes by nonthermal means.

It has been well recognized in the medical field that one of the most effective procedures in treating localized disease is to direct the treatment of that disease directly to the affected area. Some techniques in use today to deliver drugs within the body involve the utilization of time-released capsules in which drugs slowly "leak" from the capsule, or implantable "syringes" that mechanically release drugs into muscles or the blood stream. Another, and perhaps more effective delivery system, encompasses the use of liposomes containing the appropriate drug and/or chemical. The liposome encapsulated drug is then directed to the specific area of interest and the drug released. This last stop is the most problematic. Liposomes are microscopic particles which are made up of one lipid bilayer enclosing a single aqueous compartment. They are normally not leaky but can become leaky if a hole occurs in the membrane, if the membrane is dissolved or degrades, or if the membrane temperature is increased to the phase transition temperature T.

Unfortunately, as pointed out in an article by Milton B. Yatvin et. al., "Design of Liposomes for Enhanced Local Release of Drugs by Hyperthermia," *Science*, vol. 202, Dec. 22, 1978, pp 1290–1292, the major barrier to the use of liposomes as drug carriers is making the liposomes release the drugs at target sites. In both the above-identified article by Milton B. Yatvin et. al. and an article by J. N. Weinstein et. al., "Liposomes and Local Hyperthemia: Selective Delivery of Methotrexate to Heated Tumors," *Science*, vol. 204, Apr. 13, 1979, pp 188–191, the specific use of heat to raise liposome temperature to $T_c$ to make them leaky is described.

The technique as presented above still falls short as an effective drug release technique since the prolonged application of heat can, in itself, create problems within the human body, and in many instances drug release by significant liposome heating may damage body tissues to such an extent that the adverse effects of the treatment outweigh the beneficial effects of the drug being released. Therefore, the need for an effective system in which chemicals/drugs are released from liposomes without the need for heating is an important major problem in the medical industry.

SUMMARY OF THE INVENTION

The present invention overcomes the problems encountered in the past and as set forth in detail hereinabove by providing a system utilizing nonionizing electromagnetic fields trigger the localized release of chemicals and/or drugs from liposomes by nonthermal means.

I have discovered that when liposome encapsulated drugs are placed in electromagnetic fields drug release occurs without the need to heat the liposomes. The fields act to release drugs via a nonthermal mechanism. The fields may range between 26–2450 MHz (RF radiation–microwave) in order to release the drugs and/or chemicals from the liposomes. Drug release is also enhanced by oxygen and is attenuated by antioxidants.

It is clearly established, therefore, by the technique of the present invention that the permeability of liposomes is greatly increased by nonthermal interaction with nonionizing electromagnetic radiation. Consequently, the technique of the present invention is an extremely effective medical tool to rapidly deliver drugs and/or chemicals into localized areas of the human body by simply adding an electromagnetic field without the need to resort to heating.

It is therefore an object of this invention to provide an effective technique for the delivery of drugs and/or chemicals.

It is another object of this invention to provide a technique of releasing drugs and/or chemicals from liposomes by electromagnetic field stimulation.

It is still another object of this invention to provide the release of drugs and/or chemicals as a result of liposome membrane fusion.

For a better understanding of the present invention together with other and further objects thereof, reference is made to the following description taken in conjunction with the accompanying drawings and its scope will be pointed out in the appended claims.

DETAILED DESCRIPTION OF THE PREFERRED EMBODIMENT

The present invention deals with the rapid release of drugs and/or chemicals from liposomes by nonionizing electromagnetic fields. Liposomes are characteristically not leaky but can be made permeable by disrupting the membrane to the phase transition temperature, $T_c$. However, by subjecting liposomes to electromagnetic fields a new type of ion thermal interaction occurs that makes the liposome leaky, showing that membrane fusion occurs during field treatment.

Although a wide variety of liposomes are capable of use within the techniques of the present invention, the particular liposomes utilized in demonstrating the feasibility of the present invention are termed large unilamellar, or single layer, vesicles (LUV). More specifically, the LUV's employed within the technique of the present invention are made up of a 4:1 weight combination of radiolabelled dipalmitoylphosphatidylcholine (C-14-DPPC) and dipalmitoylphosphatidylglycerol (DPPG), prepared in a physiological buffer (that is, saline, 10 mM HEPES, pH 7.4). These LUV's were made by reverse phase evaporation using chloroform and isopropyl ether. Tritiated arabinofuranosidecytosine (H-3-ARA-C) was employed as a model drug-chemical and loaded into the liposomes during their formation by ultrasound. LUV's prepared in this manner, and for reasons which become more apparent later, have two radioisotope markers: H-3-ARA-C as an interior label to follow permeability changes and the release of drugs, and C-14-DPPC as a membrane label to follow changes in liposome membrane disruption.

With the present invention typical liposome release assay encompasses treating the liposomes with an electromagnetic field that does not heat the liposome, followed by rapid pelleting the liposomes at 170,000 $\times$ g to enable collection of the supernatant. The collected supernatant is then analyzed for the presence of H-3-ARA-C and C-14-DPPC by conventional liquid scintillation spectroscopy. A detailed description of the experimental procedures used with the present invention are set forth in an article co-authored by the inventor entitled "Microwave-Stimulated Drug Release from Liposomes," *Radiation Research*, 103, 266–275 (1985) and incorporated herein by reference.

Figure 1:
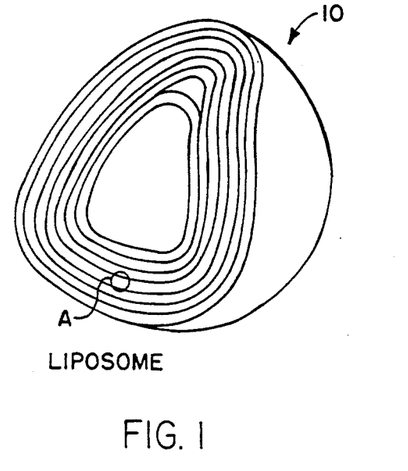
FIG. 1 is a pictorial representation of a typical liposome utilized with the drug/chemical delivery technique of the present invention.
Figure 2:
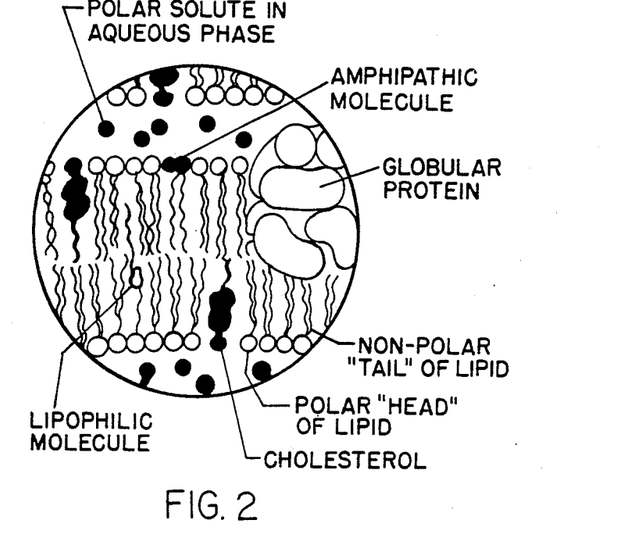
FIG. 2 is a cross-sectional representation of a portion of a single liposome bilayer membrane.

More specifically the liposomes 10 are representative of simple two-component model systems for the natural cell membrane. FIG. 1 of the drawings pictorially illustrates a typical multilayered liposome (MLV) 10, while a cross section thereof taken at A is illustrated in FIG. 2 of the drawings. As stated hereinabove, liposomes are not leaky unless the membrane is physically perturbed or the liposomes are heated to $T_c$ where the liposome 10 undergoes a phase transition and leaks molecular species trapped inside. Different components such as phospholipids, protein and cholesterol can be used to construct the liposome bilayer. Not all liposomes possess a $T_c$ where leakage occurs. A characteristic temperature $T_c$ of 39.5° C. is illustrated for the LUV's shown in FIG. 3 of the drawings for the single layer DPPC-DPPG liposomes employed. As illustrated therein such liposomes, heated in the presence of a saline buffer in a waterbath released essentially no C-14-DPPC. This indicates that the liposome membrane did not fragment during waterbath heating.

Figure 3:
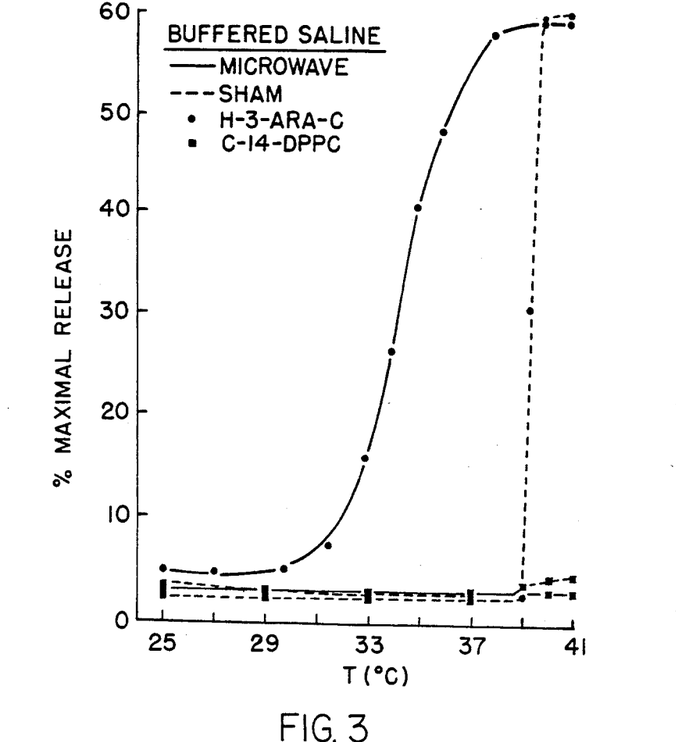
FIG. 3 is a graphic representation of drug release from a liposome in a buffered saline solution by the technique of the present invention.

Also as illustrated in FIG. 3, with the technique of the present invention, the same liposomes are subjected to a 2450 MHz electromagnetic field. This field interacts with the liposomes in a well-defined shift to a lower temperature at approximately 35° C. for drug release. Also, during such exposure there was no release of C-14-DPPC, illustrating no liposome membrane degradation.

Figure 4:
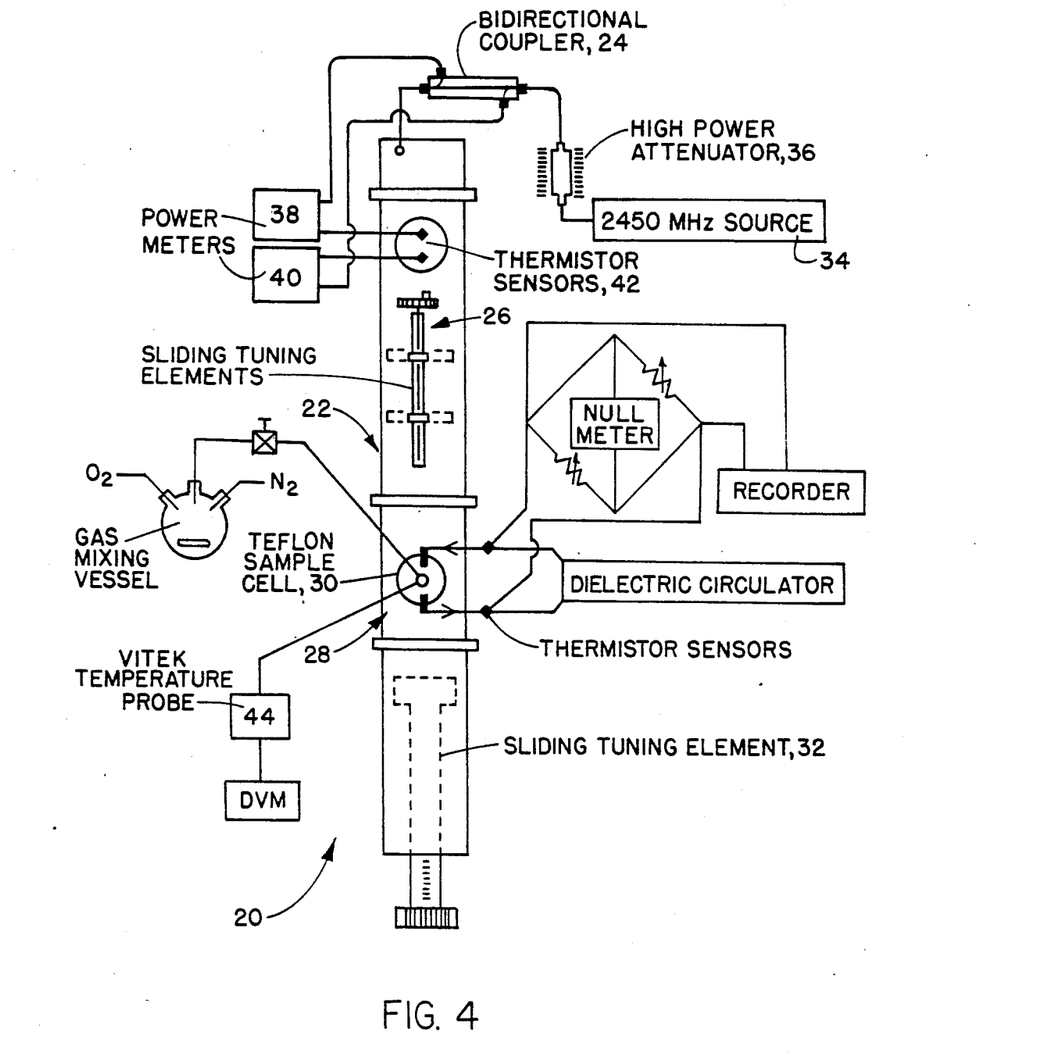
FIG. 4 is a schematic representation of an electromagnetic field exposure device utilized in the technique of the present invention.

In order to subject the liposomes to electromagnetic fields during the technique of the present invention, a microwave waveguide device 20 of the type illustrated in FIG. 4 of the drawings is utilized. This microwave waveguide device 20 is described in greater detail in a publication co-authored by the inventor and P. F. Vanek, Jr., entitled "Microwaves and the Cell Membrane. II Temperature, Plasma and Oxygen Mediate Microwave-Induced Membrane Permeability in the Erythrocyte," *Radiation Research*, 102, 190–205 (1985) and incorporated herein by reference.

More specifically device 20 generates a well-defined 2450 MHz field within a waveguide section 22. Waveguide section 22 is made up of four portions, a coaxial to cable coupler 24, an inductive/capacitive tuning element 26, an exposure section 28 incorporating therein a Teflon exposure cell 30 and a sliding short tuning element 32. The waveguide device 20 is energized by a power generator such as a Raytheon PGM-10 power generator 34 that delivers the field first to a power attenuator 36 and then through the bi-directional coupler 24. Forward and reflected power is detected in the waveguide device 20 by means of two conventional power meters 38 and 40 attached to two power sensors 42 in the inductive/capacitive tuning element section 26. The exposure cell section 28 has a port through which the Teflon exposure cell 30 is placed to expose liposomes 10 to the appropriate microwave radiation. A temperature probe 44 such as a VITEK Electrothermia Monitor that is non-perturbing to the microwave field is placed in the liposome suspension during exposure to monitor the sample temperature. In addition, 0.2 $\mu$m filtered gas (mixtures of $N_2$ and $O_2$) is bubbled (0.09 LPM) into the liposome suspension during exposures to maintain different values of $pO_2$ and to continually circulate the suspension to avoid both liposome settling and the formation of thermal hot spots.

The exposure cell 30 is temperature regulated by circulating dodecane or DOW-200 through a circulation jacket that surrounds the sample compartment. A wheatstone bridge assembly is also used to continually monitor temperature of the dielectric coolant flowing into and out of the exposure cell 30. Although the fields to which the liposomes 10 are subjected by the waveguide device 20 illustrated in FIG. 4 of the drawings is approximately 2450 MHz it should be realized that a wide range extending from 26 to 2450 MHz can effect rapid release of drugs and/or chemicals from liposomes. Power requirements for continuous wave 2450 MHz radiation is approximately 60 mW/gram of tissue for a time period ranging from less than one second to minutes based upon the desired treatment. This absorbed power requirement can be significantly reduced for sources that operate in the pulsed mode. For example a pulsed device capable of generating microwaves at approximately 26 MHz is described hereinbelow. In such a case averaged absorbed power requirements may be reduced to approximately $10^{-7}$ watts/gram of tissue.

Figure 5:
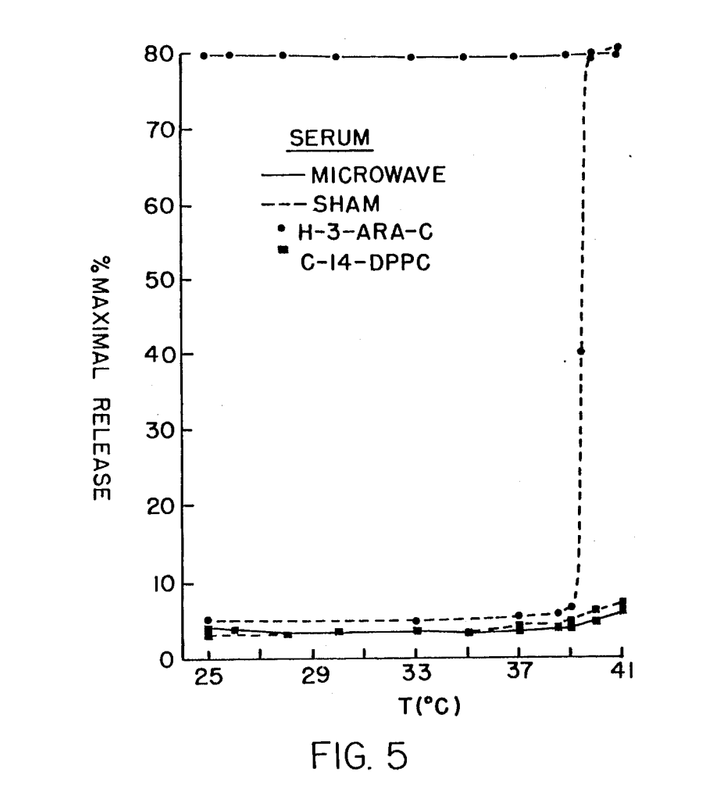
FIG. 5 is a graphic representation of drug release from a liposome in serum utilizing the technique of the present invention.

In order to substantiate that electromagnetic fields release chemicals and/or drugs from liposomes lender in vivo conditions, liposomes were exposed to fields in the presence of serum. The graph in FIG. 5 of the drawings show a characteristic drug-release curve for liposomes in serum in the presence or absence of the field. As in the graph illustrated in FIG. 3, in the absence of the field liposomes display a characteristic phase transition at $T_C = 39.5°$ C. In addition no significant release of C-14-DPPC from the liposome membrane occurs. Upon the exposure to microwaves in accordance with the technique of the present invention, a near total release of H-3-ARA-C occurs even at the lowest temperature employed. Thus the $T_N$ has been shifted to very low temperatures with the technique of the present invention. The above data also indicates that in the presence of serum, field exposure leads to a marked release of drug without liposome membrane destruction. This demonstrates that release of chemicals and/or drugs from liposomes by fields can also be accomplished in serum under conditions in vivo.

Figure 6:
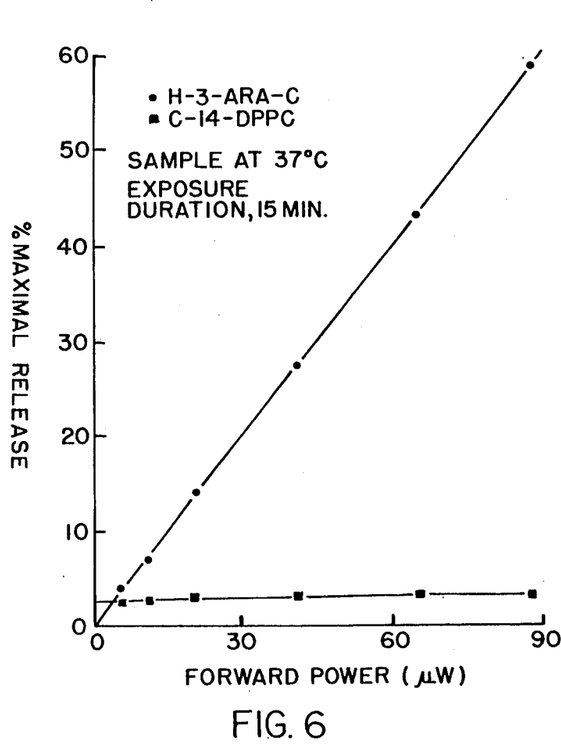
FIG. 6 is a graphic representation of dose response of drug release from a liposome as a function of absorbed power utilizing the technique of the present invention.

The dose-dependence of release of liposomes is further illustrated by varying the power deposited into the liposome suspension. FIG. 6 is a graph which illustrates the dose-response relationship. With a forward power in the waveguide device 20 increased from 3 to 100 $\mu$W, liposome release of H-3-ARA-C increased in a strictly linear fashion as shown in FIG. 6. Forward power is indicative of the absorbed dose experienced by the liposomes since reflected power was controlled to less than 1 $\mu$W by tuning the waveguide device 20 during radiations. A linear relationship between liposome release and forward power confirms that the microwave effect is monotonic and is a simple function of absorbed power of the liposome suspension.

Figure 7:
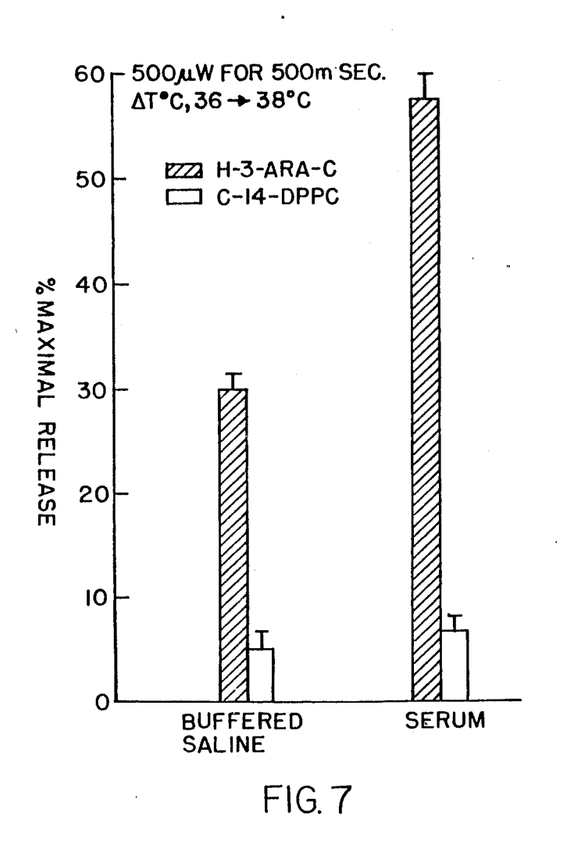
FIG. 7 is a graphic representation of the rapid release of a drug from a liposome utilizing the technique of the present invention.

In order to substantiate that liposome drug release occurs in a rapid fashion, liposome suspensions were exposed for fractions of a second to 2450 MHz fields in the presence of saline buffer or serum. FIG. 7 graphically presents data indicating that rapid release of H-3-ARA-C occurs in fractions of seconds without C-14-DPPC release in both saline buffer and serum. Significantly, rapid release is markedly enhanced when liposomes are exposed to fields in the presence of serum. This important aspect of the present invention means that field exposures that last only fractions of a second will result in near maximum liposome release under in vivo conditions.

Figure 8:
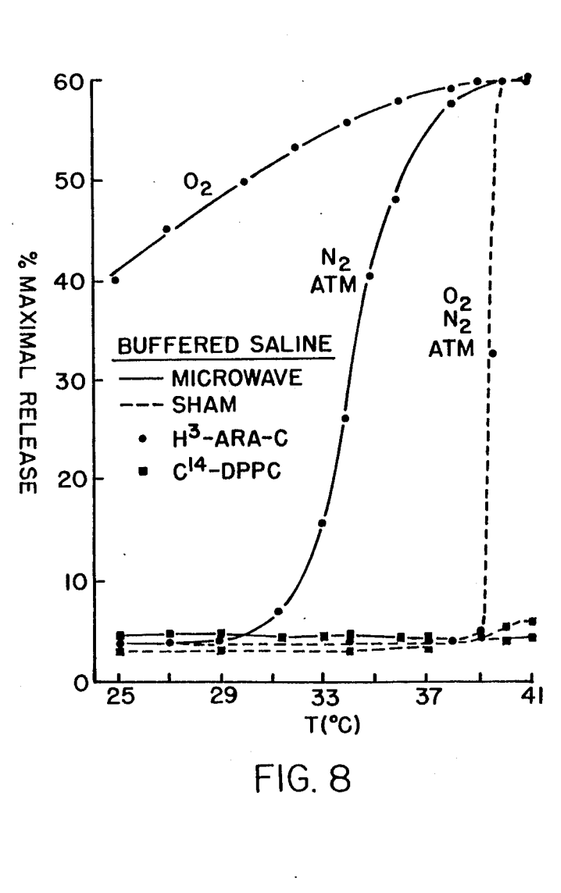
FIG. 8 is a graphic representation of the effect of $O_2$ and $N_2$ on electromagnetic release of a drug from a liposome utilizing the technique of the present invention.
Figure 9:
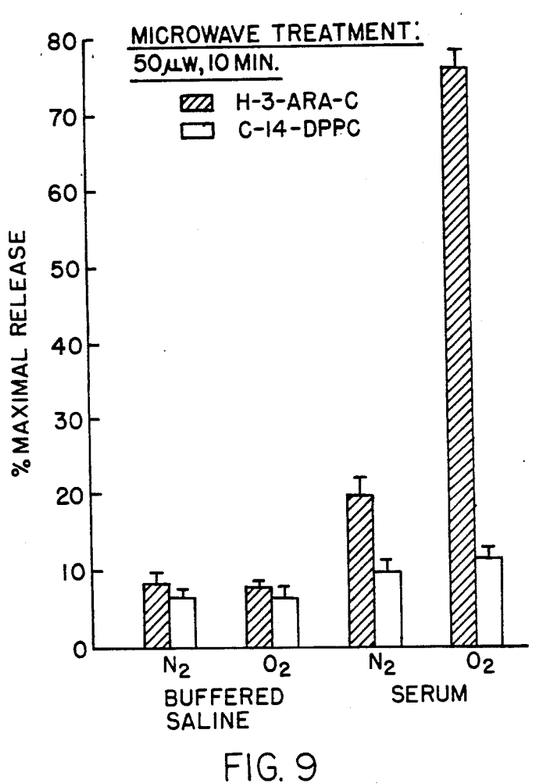
FIG. 9 is a graphic representation of the effects of $O_2$ and $N_2$ on electromagnetic release of a drug from a liposome in buffered saline and serum using the technique of this invention.

In addition, the effect of $O_2$ on electromagnetic release of liposomes is considered in the technique of this invention since $pO_2$ varies considerably in vivo. FIG. 8 of the drawings illustrates the effect of $O_2$ and $N_2$ on liposome release for liposomes in buffered saline. The introduction of $O_2$ markedly enhances field induced. This indicates that release in vivo will be more rapid in arteries where $pO_2$ is elevated, or in highly perfused tissues. Further support for this finding is illustrated in FIG. 9 of the drawings wherein liposomes are shown to respond to fields to a greater extent in the presence of serum, and the enhancing effect of $O_2$ is markedly potentiated in serum.

Consequently, the present invention provides a technique whereby a variety of liposome release a variety of drugs and/or chemicals rapidly in response to the application of nonionizing electromagnetic fields. In addition, this technique is greatly enhanced in the presence of serum and when oxygen is present. Such a technique represents a new modality that employs an electromagnetic field in a nonthermal manner to accomplish the rapid, spatially selective delivery of drugs and/or chemicals in vivo.

Figure 10:
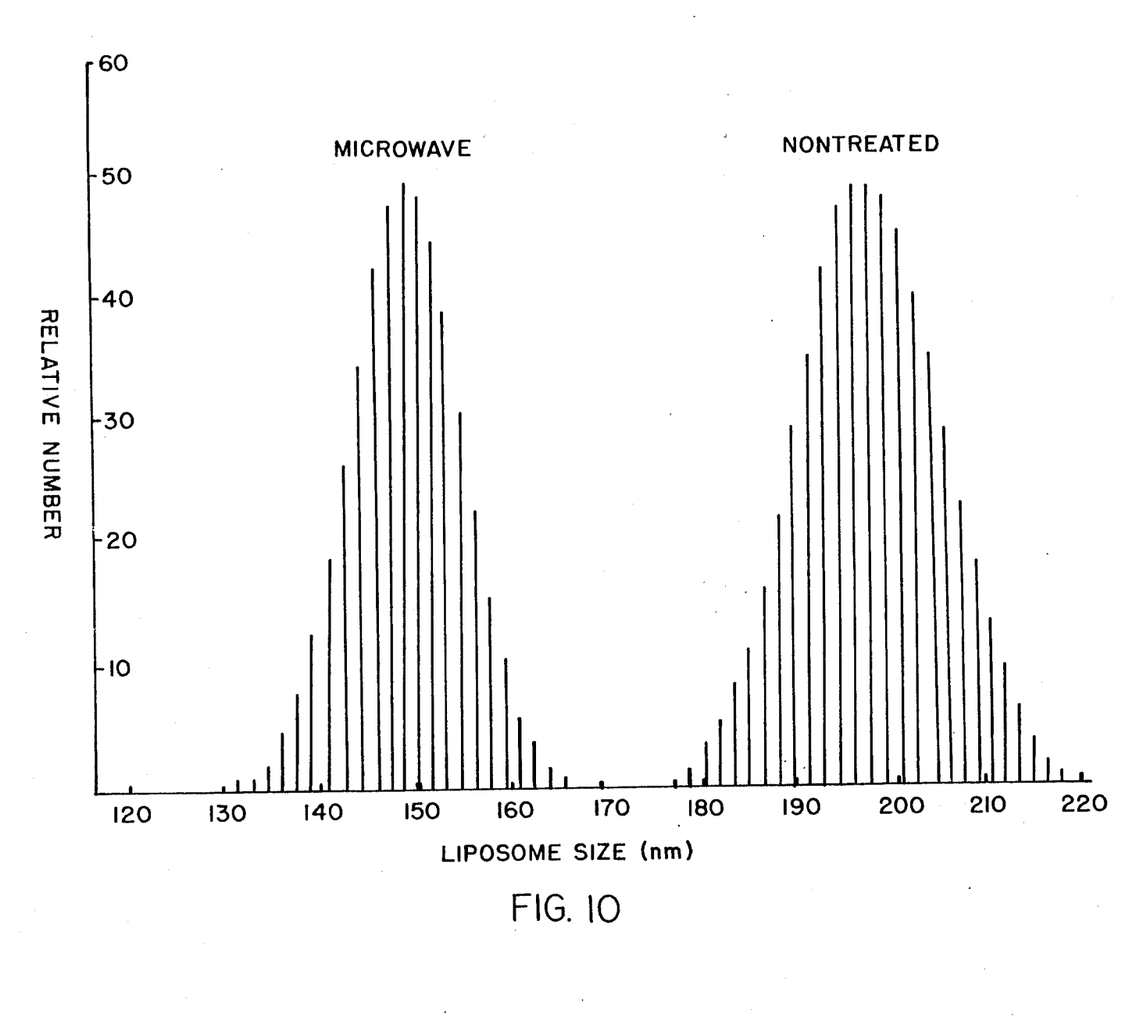
FIG. 10 is a graphic representation of the effects of electromagnetic fields on liposome size utilizing the technique of the present invention.

It has also been established as a result of the present invention that the rapid release of chemicals and/or drugs from liposomes by electromagnetic fields occurs as a result of membrane fusion. This aspect of the interaction allows the liposomes to interact with target tissues or cells to deliver drugs into the structures by fusing with them. FIG. 10 of the drawings presents laser light-scattering sizing data for the liposomes before and after exposure to 2450 MHz fields. The non-treated liposomes were approximately 200 nm in diameter and were maintained in a water bath at 39.5° C. Other liposomes also of 200 nm diameter were exposed to 2450 MHz fields at 39.5° C. for 20 minutes. Also the liposomes (untreated and field treated) were then analyzed for size distribution on a conventional particle size distribution device such as a NICOMP 200 Laser Particle Size Distribution Device. The results indicate that field treatment reduces the size of the liposomes.

For example, the 200 nm liposomes reduced to approximately 150 nm in diameter after field treatment while the untreated liposomes remained substantially the same size. This means that the vesicles underwent a membrane fusion or division to form smaller vesicles. This effect explains the drug release observed during field exposure during the technique of the present invention. In addition, similar results were also observed when liposomes were field treated over the range of 39°-42° C.

Figure 11:
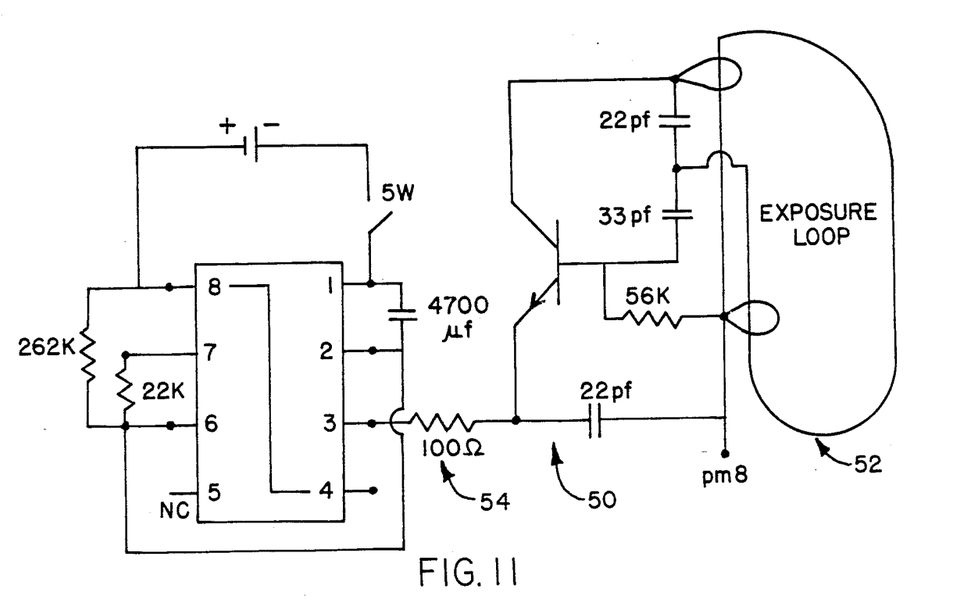
FIG. 11 is an alternate electromagnetic exposure device utilized with the technique of the present invention.
Figure 12:
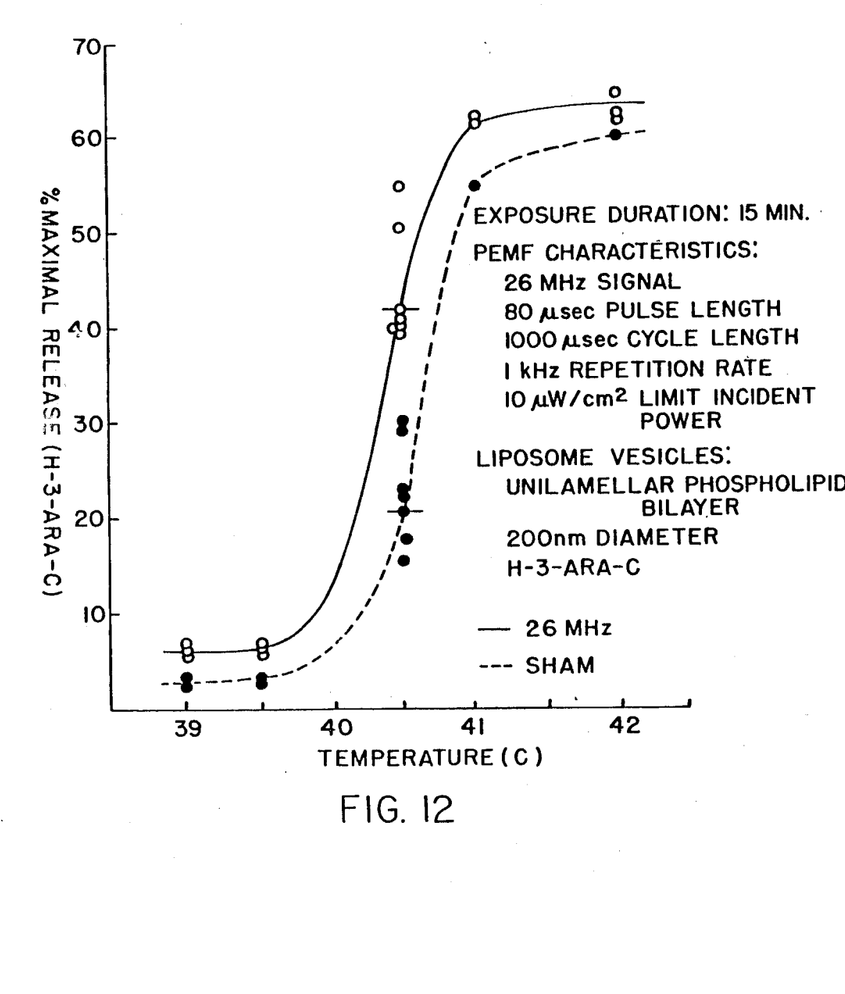
FIG. 12 is a graphic representation of increased liposome permeability in liposome membranes subjected to 26MHz fields utilizing the technique of the present invention.

In addition to the exposure of liposomes by 2450 MHz fields in the manner presented hereinabove, liposomes can also be exposed to lower frequency electromagnetic fields of, for example, 26 MHz. For such exposure, a device 50 of the type illustrated in FIG. 11 of the drawings can be utilized. This type of generating device 50 incorporates therein a small radiating antenna loop 52. To conduct the field exposure, loop 52 is placed into a water bath to establish and control at a specific temperature, and liposomes are placed in the center of loop 52 in a small plastic tube of 20 mm$\times$7 mm. Loop 52 is activated by circuit 54 and after exposure to the low frequency field, analysis of the liposomes for drug release yields the graphic representation of FIG. 12. The results indicate that the field can induce release of drug, compared to the case for no fields. Consequently, it is possible to rapidly increase the drug and/or chemical release from liposomes by subjecting the liposomes to a wide range of electromagnetic field exposure from, for example, 26 to 2450 MHz.

Figure 13:
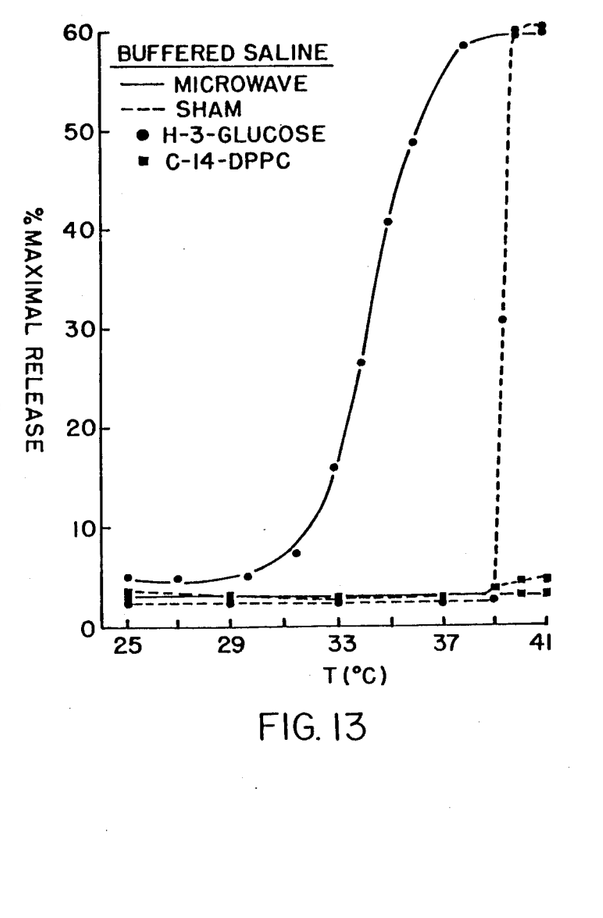
FIG. 13 is a graphic representation of release of glucose loaded liposomes utilizing the technique of the present invention.

Although the analysis presented hereinabove refers to the release of a particular drug arabinofuranoside cytosine (ARA-C), the rapid release of a variety of different drugs and/or chemicals can be effected by the exposure of liposomes to electromagnetic fields. In order to substantiate this analysis, glucose was substituted for ARA-C in a batch of LUV liposomes. Results from the drug release of glucose is illustrated in the graph of FIG. 13 of the drawings. H-3-Glucose was released from the liposomes at much lower temperatures in microwave-treated samples while the C-14 labeled liposome membrane (C-14-DPPC) did not experience any fragmentation and release of lipid. Thus, although the chemical or drug was released, the membrane itself was not disrupted. Such an analysis substantiates the results derived from the technique of this invention that drugs, in general, can be placed into liposomes and then released upon exposure to electromagnetic fields.

It is pointed out once again that the utilization of the C-14-labeled DPPC mentioned above is extremely important in analysis of the present invention because it is placed in the liposome membrane, and will not be released into the supernatant unless the liposome membrane is physically disrupted. Since no radiolabeled DPPC was detected in the supernatant by the use of the present invention it is verified that the drug release occurs not as a result of membrane disruption but as a result of membrane fusion wherein the release of drugs takes place without the release of membrane fragments.

During actual "human-use" of the technique of the present invention, liposomes loaded with a drug can be injected directly into the blood stream of an individual. Once injected, the specific area of the human body to be treated with the drug is exposed to an electromagnetic field thereby effecting release of the drug to the specific area in need of treatment. The device utilized with human beings could be slightly diffent than the generating devices 20 and 50 depicted in FIGS. 4 and 11 of the drawings. Although the same field described hereinabove with respect to devices 20 and 50 is utilized, a small conventionally available radiating antenna would be utilized to focus the radiation to a particular area of the human body.

As an alternative approach utilizing the technique of the present invention it is also possible to inject the liposomes directly into specific tissues of the body. With such an approach the specific tissue is then subjected to the electromagnetic field in order to effect the rapid release of drugs therein.

Although this invention has been described with reference to a particular embodiment, it will be understood that this invention is also capable of further and other embodiments within the spirit and scope of the appended claims.

I claim:

1. A method of delivering a chemical agent to a preselected area of a body, comprising the steps of:
   (a) encapsulating said chemical agent within a liposome, said liposome having a predetermined phase transition temperature at which said liposome is capable of releasing said chemical agent;
   (b) injecting said liposome into the blood stream of said body; and
   (c) subjecting said preselected area of said body to nonionizing electromagnetic fields without heating said preselected area of said body to said predetermined phase transition temperature in order to release said chemical agent from said liposome by nonthermal means at a temperature below said predetermined phase transition temperature.

2. A method of delivering a chemical agent to a preselected area of a body as defined in claim 1 further comprising the step of ensuring that said liposome is impermeable prior to subjecting said liposome to said electromagnetic fields.

3. A method of delivering a chemical agent to a preselected area of a body as defined in claim 2 wherein said electromagnetic fields are in the range of 26-2450 MHz.

4. A method of delivering a chemical agent to a preselected area of a body as defined in claim 3 wherein said preselected area of said body is subjected to said electromagnetic fields for periods of time as short as one second and at a power of approximately 60 mW/gram of tissue at said preselected area of said body.

5. A method of delivering a chemical agent to a preselected area of a body as defined in claim 4 wherein said liposome is a unilamellar vesicle.

6. A method of delivering a chemical agent to a preselected area of a body as defined in claim 5 wherein said unilamellar vesicle is made up of 4:1 weight combination of dipalmitoylphosphatidylcholine and dipalmitoylphosphatidylglycerol prepared in a physiological buffer.

7. A method of delivering a chemical agent to a preselected area of a body as defined in claim 1 wherein said release of said chemical agent is enhanced by injecting serum into said preselected area of said body.

8. A method of delivering a chemical agent to a preselected area of a body as defined in claim 1 wherein said release of said chemical agent is enhanced by introducing oxygen into said preselected area of said body.

9. A method of delivering a chemical agent to a preselected area of said body as defined in claim 8 wherein said release of said chemical agent is enhanced by injecting serum into said preselected area of said body.

10. A method of delivering a chemical agent to a preselected area of a body, comprising the steps of:
    (a) encapsulating said chemical agent within a liposome, said liposome having a predetermined phase transition temperature at which said liposome is capable of releasing said chemical agent;
    (b) injecting said liposome into a preselected tissue of said body; and
    (c) subjecting said preselected tissue of said body to nonionizing electromagnetic fields without heating said tissue to said predetermined phase transition temperature in order to release said chemical agent from said liposome by nonthermal means at a temperature below said predetermined phase transition temperature.

11. A method of delivering a chemical agent to a preselected area of said body as defined in claim 10 further comprising the step of ensuring that said liposome is impermeable prior to subjecting said liposome to said electromagnetic fields.

12. A method of delivering a chemical agent to a preselected area of a body as defined in claim 11 wherein said electromagnetic fields are in the range of $26 \geqq 2450$ MHz.

13. A method of delivering a chemical agent to a preselected area of a body as defined in claim 12 wherein said preselected area of said body is subjected to said electromagnetic fields for periods of time as short as one second and at a power of approximately 60 mW/gram of tissue at said preselected area of said body.

14. A method of delivering a chemical agent to a preselected area of said body as defined in claim 13 wherein said liposome is a unilamellar vesicle.

15. A method of delivering a chemical agent to a preselected area of a body as defined in claim 14 wherein said unilamellar vesicle is made up of 4:1 weight combination of dipalmitoylphosphatidylcholine and dipalmitoylphosphatidylglycerol prepared in a physiological buffer.

16. A method of delivering a chemical agent to a preselected area of said body as defined in claim 10 wherein said release of said chemical agent is enhanced by injecting serum into said preselected area of said body.

17. A method of delivering a chemical agent to a preselected area of said body as defined in claim 10 wherein said release of said chemical agent is enhanced by introducing oxygen into said preselected area of said body.

18. A method of delivering a chemical agent to a preselected area of said body as defined in claim 17 wherein said release of said chemical agent is enhanced by injecting serum into said preselected area of said body.

* * * * *

UNITED STATES PATENT AND TRADEMARK OFFICE
CERTIFICATE OF CORRECTION

PATENT NO. : 4,801,459

DATED : January 31, 1989

INVENTOR(S) : Robert P. Liburdy

It is certified that error appears in the above-identified patent and that said Letters Patent is hereby corrected as shown below:

Column 1, line 35, the term "T" should be changed to -- $T_c$ --.

Column 1, line 64, insert after "fields" the word -- to --.

Column 2, line 14, change "adding" to -- applying --.

Column 3, line 15, change "ion" to -- non --.

Column 5, line 4, change "lender" to -- under --.

Column 5, line 23, change the position of "conditions" from in front of "in vivo" to after "in vivo".

Column 5, line 56, insert after "induced" the term -- release --.

Signed and Sealed this

Fifth Day of September, 1989

*Attest:*

DONALD J. QUIGG

*Attesting Officer*  *Commissioner of Patents and Trademarks*